United States Patent
Gliner

(10) Patent No.: US 10,643,330 B2
(45) Date of Patent: May 5, 2020

(54) REGISTRATION OF AN ANATOMICAL IMAGE WITH A POSITION-TRACKING COORDINATE SYSTEM BASED ON PROXIMITY TO BONE TISSUE

(71) Applicant: Biosense Webster (Israel) Ltd., Yokneam (IL)

(72) Inventor: Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 42 days.

(21) Appl. No.: 15/493,703

(22) Filed: Apr. 21, 2017

(65) Prior Publication Data
US 2018/0308232 A1    Oct. 25, 2018

(51) Int. Cl.
   G06T 7/00    (2017.01)
   A61B 6/00    (2006.01)
   (Continued)

(52) U.S. Cl.
   CPC ............ *G06T 7/0012* (2013.01); *A61B 5/061* (2013.01); *A61B 5/062* (2013.01); *A61B 5/065* (2013.01); *A61B 6/032* (2013.01); *A61B 6/5211* (2013.01); *A61B 6/547* (2013.01); *A61B 34/20* (2016.02); *G01B 7/004* (2013.01); *G06T 7/33* (2017.01);
   (Continued)

(58) Field of Classification Search
   CPC ......... G06T 7/0012; G06T 7/33; A61B 34/20; A61B 5/061; A61B 5/062; A61B 5/065; A61B 6/032; A61B 6/5211; A61B 6/547
   See application file for complete search history.

(56) References Cited

U.S. PATENT DOCUMENTS

| 5,391,199 A | 2/1995 | Ben-Haim |
| 6,239,724 B1 | 5/2001 | Doron et al. |

(Continued)

FOREIGN PATENT DOCUMENTS

| WO | WO9605768 | 2/1996 |
| WO | WO 2015/024600 | 2/2015 |

OTHER PUBLICATIONS

European Search Report dated Sep. 17, 2018 from corresponding European Patent Application No. 18168409.3.
(Continued)

*Primary Examiner* — Kim Y Vu
*Assistant Examiner* — Molly Delaney
(74) *Attorney, Agent, or Firm* — Todd J. Burns

(57) ABSTRACT

A method includes, identifying, in a three-dimensional (3D) anatomical image of a patient organ, multiple anatomical points corresponding to respective predefined locations on a skin of the patient organ in a first coordinate system. Multiple positions in a second coordinate system, measured by a position sensor of a position-tracking system at the respective predefined locations on the skin of the patient organ, are received. At each predefined location, a distance is calculated between a respective anatomical point and closest bone tissue of the patient organ. Weights are assigned to the predefined locations based on respective distances between the anatomical points and the closest bone tissue. The first and second coordinate systems are registered, by correlating between the positions and the respective anatomical points using the assigned weights.

11 Claims, 3 Drawing Sheets

(51) Int. Cl.
*A61B 5/06* (2006.01)
*G01B 7/004* (2006.01)
*A61B 34/20* (2016.01)
*A61B 6/03* (2006.01)
*G06T 7/33* (2017.01)
*A61B 17/24* (2006.01)

(52) U.S. Cl.
CPC ....... *A61B 17/24* (2013.01); *A61B 2034/2051* (2016.02); *A61B 2034/2072* (2016.02); *G06T 2207/10081* (2013.01); *G06T 2207/30008* (2013.01); *G06T 2207/30088* (2013.01); *G06T 2207/30201* (2013.01)

(56) References Cited

U.S. PATENT DOCUMENTS

| | | | |
|---|---|---|---|
| 6,332,089 B1 | 12/2001 | Acker et al. | |
| 6,484,118 B1 | 11/2002 | Govari | |
| 6,560,354 B1 * | 5/2003 | Maurer, Jr. | G06T 7/33 128/922 |
| 6,618,612 B1 | 9/2003 | Acker et al. | |
| 6,690,963 B2 | 2/2004 | Ben-Haim et al. | |
| 8,271,068 B2 | 9/2012 | Khamene et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2008/0269602 A1 | 10/2008 | Csavoy et al. | |
| 2012/0004541 A1 | 1/2012 | Yamamoto et al. | |
| 2014/0193053 A1 | 7/2014 | Kadoury et al. | |
| 2015/0157416 A1 * | 6/2015 | Andersson | A61B 17/1757 606/102 |
| 2016/0242934 A1 * | 8/2016 | van der Walt | A61F 2/4684 |

OTHER PUBLICATIONS

Rusinkiewicz et al., "Efficient Varients of the ICP Algorithm", proceedings of the third international conference on 3-D Digital Imaging and Modeling (2005).

Chen et al., "Object Modeling by Registration of Multiple Range Images" proceedings ofthe IEEE conference on Robotics and Automation, pp. 2724-2729, vol. 3, 1991.

* cited by examiner

REGISTRATION OF AN ANATOMICAL IMAGE WITH A POSITION-TRACKING COORDINATE SYSTEM BASED ON PROXIMITY TO BONE TISSUE

FIELD OF THE INVENTION

The present invention relates generally to registration of coordinate systems, and particularly to methods and systems for registering coordinate systems based on proximity to a stationary organ.

BACKGROUND OF THE INVENTION

Computerized tomography imaging systems and position-tracking systems may be used in various medical applications, such as image guided procedures.

For example, U.S. Pat. No. 6,560,354, whose disclosure is incorporated herein by reference, describes apparatus and method for registration of images to physical space using a weighted combination of points and surfaces. An image of a patient taken through X-ray computed tomography is registered to physical measurements taken on the patient's body. Different parts of the patient's body are given different numerical weights; for example, if bone measurements are deemed to be more accurate than skin measurements, the bones can be given a higher weight than the skin. The weights are used in an iterative registration process to determine a rigid body transformation function.

U.S. Pat. No. 8,271,068, whose disclosure is incorporated herein by reference, describes a method of determining a three-dimensional (3D) position of a catheter tip that includes: compensating a two-dimensional (2D) position of the tip of the catheter for respiratory motion to generate a compensated 2D catheter position, generating weighted sample points around the compensated 2D catheter position, determining correspondent points of the weighted sample points in a 3D image, computing a weighted mean and a weighted covariance of each correspondent point, and determining the 3D position of the catheter tip in the 3D image from a fusion of the weighted means and weighted covariance.

SUMMARY OF THE INVENTION

An embodiment of the present invention that is described herein provides a method that includes identifying, in a three-dimensional (3D) anatomical image of a patient organ, multiple anatomical points corresponding to respective predefined locations on a skin of the patient organ in a first coordinate system. Multiple positions in a second coordinate system, measured by a position sensor of a position-tracking system at the respective predefined locations on the skin of the patient organ, are received. At each predefined location, a distance is calculated between a respective anatomical point and closest bone tissue of the patient organ. Weights are assigned to the predefined locations based on respective distances between the anatomical points and the closest bone tissue. The first and second coordinate systems are registered, by correlating between the positions and the respective anatomical points using the assigned weights.

In some embodiments, assigning the weights includes assigning a first weight to a first predefined location having a first distance to the closest bone tissue, and assigning a second weight, larger than the first weight, to a second predefined location having a second distance to the closest bone tissue, smaller than the first distance, and registering the first and second coordinate systems includes calculating a transformation between the first and second coordinate systems, in which the second predefined location has higher impact than the first predefined location. In other embodiments, the 3D anatomical image includes a computerized tomography (CT) anatomical image. In yet other embodiments, the patient organ includes a patient head, and receiving the multiple positions includes receiving positions located at the predefined locations on the patient head.

In an embodiment, receiving the multiple positions includes receiving the positions from a registration tool that includes the position sensor. In another embodiment, calculating the distance includes calculating a Euclidean distance vector having multiple components. In yet another embodiment, assigning the weights includes assigning a weight to each respective component of the Euclidean distance vector, and registering the first and second coordinate systems includes using, at each predefined location, the assigned weights to each of the respective components.

There is additionally provided, in accordance with an embodiment of the present invention, an apparatus that includes a registration tool and a processor. The registration tool includes a position sensor of a position-tracking system, which is configured to acquire multiple positions in a second coordination system by positioning the registration tool at respective predefined locations on a skin of a patient organ. The processor is configured to identify, in a three-dimensional (3D) anatomical image of the patient organ, multiple anatomical points corresponding to the respective predefined locations in a first coordinate system, to receive the multiple positions measured in the second coordinate system, to calculate, at each predefined location, a distance between a respective anatomical point and closest bone tissue of the patient organ, to assign weights to the predefined locations based on respective distances between the anatomical points and the closest bone tissue, and to register the first and second coordinate systems, by correlating between the positions and the respective anatomical points using the assigned weights.

The present invention will be more fully understood from the following detailed description of the embodiments thereof, taken together with the drawings in which:

DETAILED DESCRIPTION OF EMBODIMENTS

Overview

Figure 1:
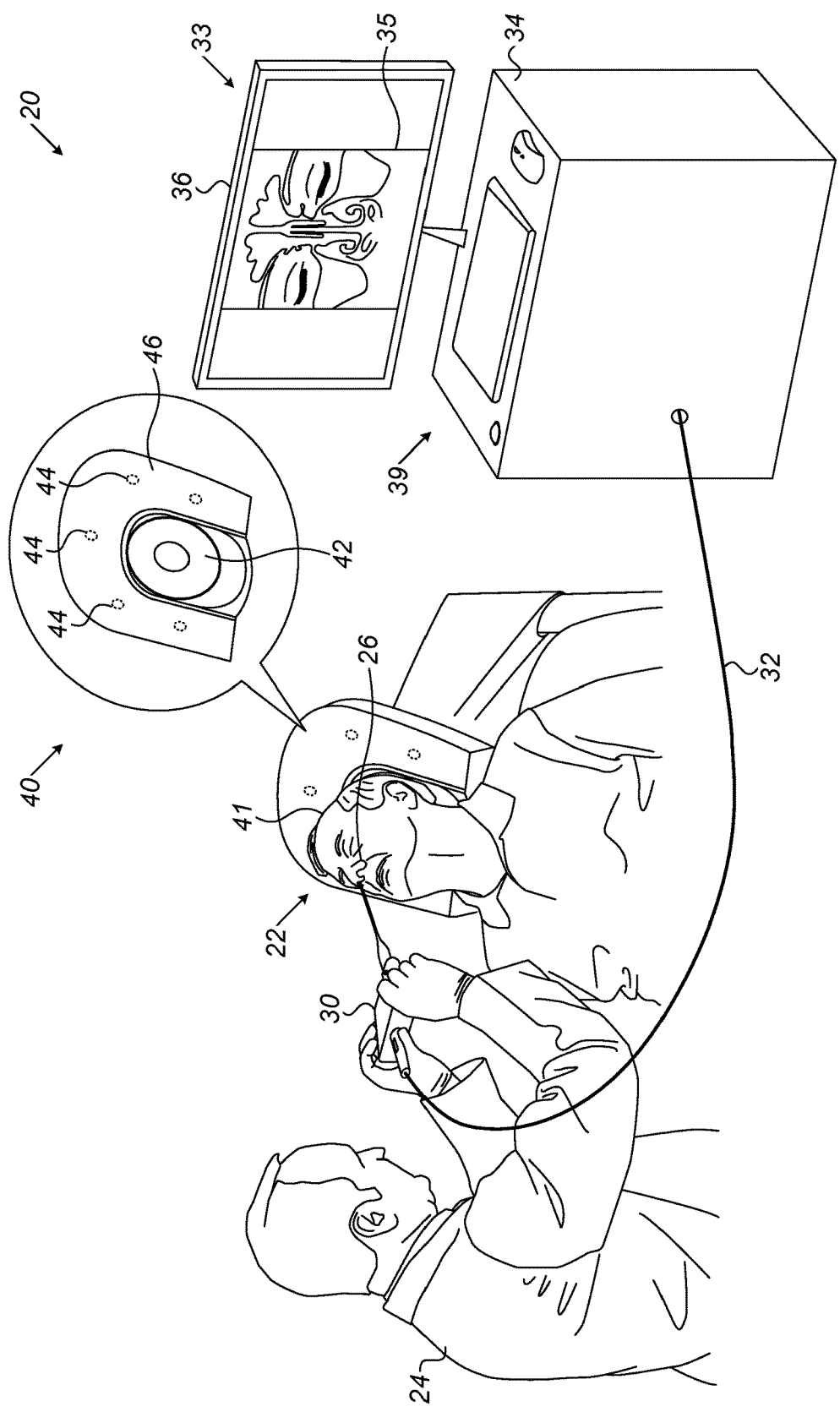
FIG. 1 is a schematic, pictorial illustration of a sinuplasty surgical system, in accordance with an embodiment of the present invention.

Some medical procedures, such as sinuplasty, may involve registration of an anatomical image of relevant organs with a coordinate system of a position tracking system. Using the registration, a surgical tool fitted with a position sensor may be navigated to the treated organs, and can be visualized overlaid on the anatomical image. In principle, pre-operative registration may be carried out using an external registration tool fitted with a position sensor of the position tracking system. Such a tool could be attached to preselected locations on the patient face (e.g., forehead, and centers of the two cheeks). The anatomical image could then be registered to the coordinate system of the position tracking system based on the measured positions of tissue at the preselected locations.

This possible solution, however, is likely to be inaccurate and unsuitable for sinuplasty procedures, in which it is typically important to obtain registration of the anatomical image at accuracy level better than 1 mm. Since some facial elements may comprise soft tissue that deform naturally, and because of the uncontrolled pressure applied on the tissue by the registration tool, the accuracy of this hypothetical solution may become unacceptable.

Embodiments of the present invention that are described hereinbelow provide improved techniques for registering between a coordinate system of an anatomical imaging system and a coordinate system of a position-tracking system. In the disclosed embodiments, a three-dimensional (3D) anatomical image of a patient head is acquired using a computerized tomography (CT) system. The anatomical image comprises anatomical points that are measured in a coordinate system of the CT, and should be mapped to a coordinate system of a position-tracking system.

In some embodiments, mapping between the two coordinate systems is carried out using a registration tool that comprises a position sensor of the position-tracking system. In order to perform the registration, a physician attaches the distal end of the registration tool to multiple predefined locations on a skin of the patient face. At each of the predefined locations, the position tracking system measures the position of the position sensor (and thus of the predefined location) in its own coordinate system.

In some embodiments, the anatomical image is provided to a processor, which identifies the predefined locations in the anatomical image, and calculates (in the CT coordinate system) for each predefined location, a distance between the anatomical point corresponding to the predefined location and the closest point on a bone tissue of the patient face.

The distance from skin to bone may vary across the head surface. On the forehead, for example, the minimal distance between the anatomical point and bone tissue is substantially shorter than in the cheeks. The position measurement of predefined locations at the forehead is therefore expected to be more accurate than at the cheeks.

In some embodiments, the processor is configured to assign weights to the predefined locations based on the respective distances between the anatomical points and the closest bone tissue. In the example of the forehead and cheeks, the processor will assign higher weight values to predefined locations at the forehead than at the cheeks.

In some embodiments, the processor is configured to register the coordinate systems of the CT to the position tracking systems, by correlating between the positions acquired by the registration tool and the respective anatomical points of the image acquired by the CT. In an embodiment, the processor carries out the registration using the respective weights, by applying a suitable registration method, such as the iterative closest point (ICP) method. The registration process typically estimates a transformation between the two coordinate systems, in which measurements at locations having small distance to the closest bone tissue are given high weight, and vice versa.

Due to their high accuracy, the disclosed techniques enable, for example, improved navigation of a sinuplasty surgical tool, which is inserted into the patient head and comprises another position sensor of the position-tracking system.

System Description

FIG. 1 is a schematic pictorial illustration of a sinuplasty surgical system 20, in accordance with an embodiment of the present invention. System 20 comprises a magnetic position tracking system, which is configured to track the position of one or more position sensors in the head of a patient 22. The magnetic position tracking system comprises magnetic field-generators and one or more position sensors. The position sensors generate position signals in response to sensed external magnetic fields from the field generators, thereby enabling a processor 34 to map the position of each sensor in the coordinate system of the position tracking system as will be described below.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In the present example, system 20 comprises a location pad 40, which comprises multiple field-generators 44 fixed on a frame 46. In the exemplary configuration shown in FIG. 1, pad 40 comprises five field-generators 44, but any other suitable number of generators 44 can be used. Pad 40 further comprises a pillow 42 placed under a head 41 of patient 22, such that generators 44 are located at fixed, known positions external to the patient. System 20 further comprises a console 33, which comprises a driver circuit (not shown) configured to drive field-generators 44 with suitable signals so as to generate magnetic fields in a predefined working volume around head 41.

In some embodiments, system 20 comprises a registration tool, such as a handheld wand 30, which is used by system 20 for registering the coordinate system of the magnetic position tracking system with that of a pre-acquired computerized tomography (CT) image. The registration tool is configured to acquire position measurements, and is depicted in detail in FIG. 2 below.

In an embodiment, processor 34 is typically a general-purpose computer comprising suitable front end and interface circuits for receiving data from external sources, as well as measurements from the position sensor of wand 30, via a cable 32, and for controlling other components of system 20. Console 33 further comprises input devices 39 and a user display 36, which is configured to display the data.

Typically, a physician 24 attaches wand 30 sequentially to multiple predefined locations on an external surface of patient head 41. Each predefined location is typically chosen to be an easily identifiable feature on head 41, a forehead, a bridge of a nose 26 (located between the eyes of patient 22), a cheek, or any other suitable identifiable feature. The predefined locations are depicted in detail in FIG. 2 below.

In an embodiment, processor 34 receives a computerized tomography (CT) image 35 obtained using an external CT system (not shown). Processor 34 uses image 35 to form a surface image of at least part of patient head 41. In some embodiments, processor 34 may distinguish between different types of tissue in the CT image, and in particular identify skin and bone tissue, using any suitable criterion or technique, such as hounsfield units (HU).

In an embodiment, when placed at a predefined location on the patient head, wand 30 is configured to generate position signals indicative of the position of this predefined location in the coordinate system of the magnetic position tracking system. The acquisition of the bone tissue measurements by wand 30 is described in detail in FIG. 2 below.

In some embodiments, processor 34 is configured to calculate two coordinates for each predefined location on the patient head—an "anatomical point" in a coordinate system of the CT system, and a "position" in a coordinate system of the position tracking system. The position is derived from the position measurements of wand 30 at this predefined location, and is indicative of the coordinate of the skin at this location in the coordinate system of the magnetic position tracking system. The anatomical point is indicative of the coordinate of the skin at this location, as identified in the CT image.

In an embodiment, processor 34 is configured to correlate between the anatomical points and the positions of the predefined locations in image 35, so as to register the CT image with the coordinate system of the position tracking system.

The registration process is typically performed before the actual sinuplasty procedure. During the sinuplasty procedure, physician 24 may insert into head 41 a medical device (not shown), such as a sinuplasty catheter or other surgical tool, which comprises an additional position sensor of the position tracking system. Since the CT image is already registered with the position-tracking system, physician 24 may navigate the medical device whose distal end is displayed on the CT image, to a target location in head 41.

In alternative embodiments, instead of CT image 35, processor 34 is configured to receive one or more images acquired using another suitable anatomical imaging technique, such as fluoroscopy or magnetic resonance imaging (MM), and to register these anatomical images with the coordinate system as described above.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Registering Anatomical Image with a Position-Tracking System

Figure 2:
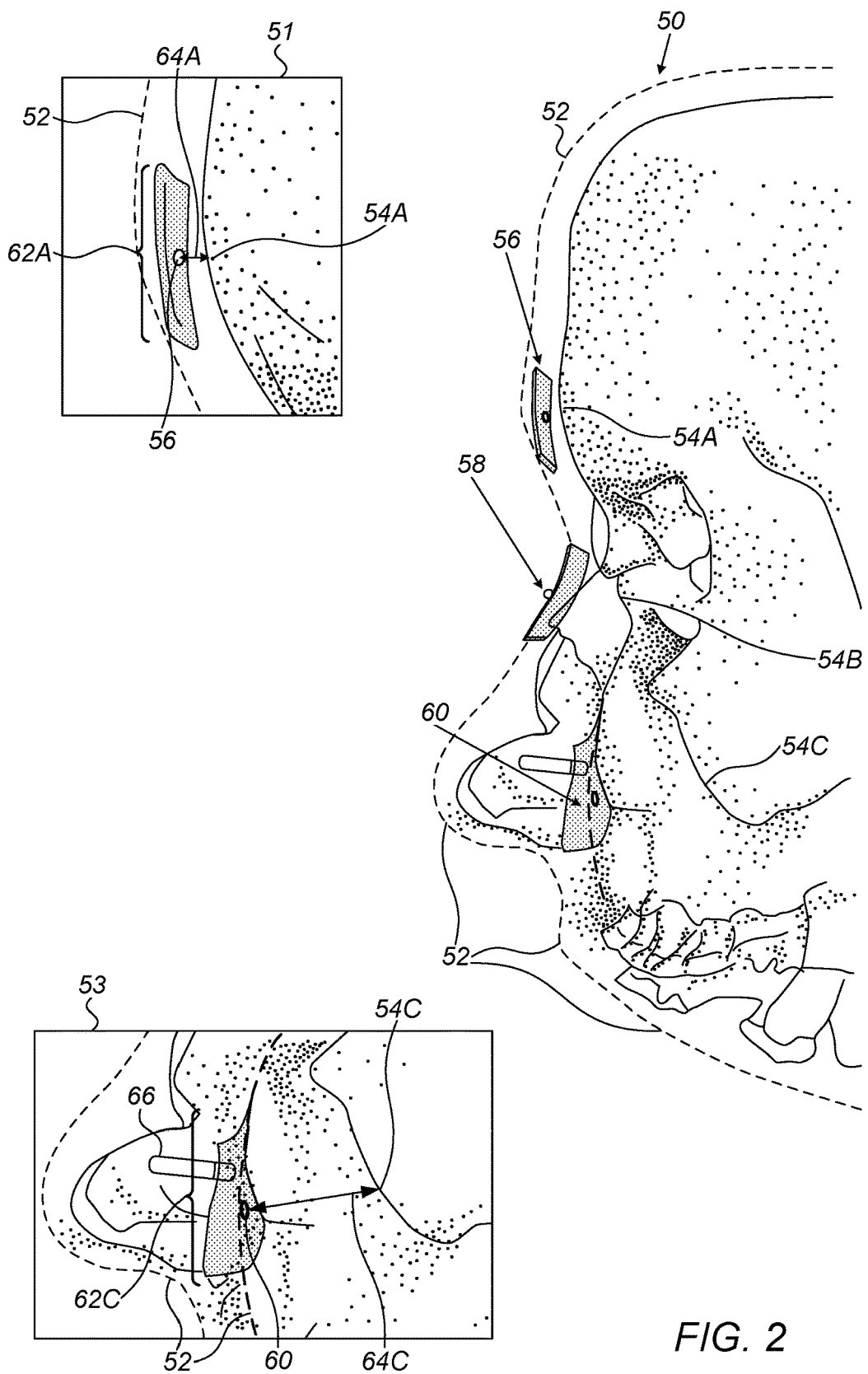
FIG. 2 is a schematic, pictorial illustration of measurement points overlaid on an anatomical image of a patient face, in accordance with an embodiment of the present invention.

FIG. 2 is a schematic, side view illustration of a three-dimensional (3D) anatomical image 50 of a patient face, in accordance with an embodiment of the present invention. Image 50 may replace, for example, image 35 of FIG. 1 above.

In some embodiments, processor 34 is configured to display image 50 using a 3D anatomical image acquired by the external CT system, or using any other suitable anatomical imaging system as described in FIG. 1 above.

In some embodiments, image 50 depicts a skin 52 of patient 22 (shown as a dashed line) and bone tissue, such as bones 54A, 54B and 54C of respective forehead, nose-bridge and cheek of patient 22.

FIG. 2 depicts in image 50 multiple predefined locations on skin 52, such as a location 56 at the forehead, a location 58 at the nose-bridge, and a location 60 at the cheek.

Reference is now made to an inset 51 showing the anatomy and measurements acquired at predefined location 56. In an embodiment, physician 24 applies wand 30 on the skin of the forehead of patient 22, so as to obtain the position of location 56 in the coordinate system of the position tracking system, using the position sensor of wand 30.

In some embodiments, processor 34 is configured to display a frame of reference comprising multiple anatomical points, referred to as CT points 62A, acquired by the CT system. In the description that follows, for the sake of clarity, the terms "anatomical points" and "CT points" are used interchangeably. CT points 62A are located on skin 52 of the forehead of patient 22, in close proximity to location 56.

In some embodiments, processor 34 is configured to identify predefined location 56 in image 50, and to select a CT point 62A, which is closest to location 56. Processor 34 is further configured to calculate a minimal distance 64A between the selected CT point 62A and bone 54A, i.e., the distance to a point on bone 54A, which is the closest bone tissue to the identified location 56 over the bone tissue of the patient face.

In the description that follows, for the sake of clarity, the terms "distance" and "distance vector" are used interchangeably.

Reference is now made to an inset 53 showing the anatomy and measurements carried out at predefined location 60. In some embodiments, processor 34 is configured to display CT points 62C located on skin 52, bone 54C, and a display 66 of wand 30. Processor 34 is further configured to identify a CT point 62C located in close proximity to predefined location 60, and to calculate a distance 64C between the identified CT point 62C and bone 54C, which is the closest bone tissue to predefined location 60.

As shown in the example of FIG. 2, distance 64C includes the thickness of skin 52 and soft tissue of the cheek of patient 22, and therefore, appears to be substantially longer than distance 64A, which includes mostly the thickness of skin 52 alone.

The face of patient 22 comprises stiff tissue, such as bones 54A, 54B and 54C, and soft tissue, such as skin 52 and flesh that resides between the skin and the respective bone. It will be understood that as physician 22 attaches wand 30 sequentially to skin 52 at the predefined locations, the uncontrolled pressure applied by the distal tip of wand 30 may deform skin 52. As a result, the position acquired for a predefined location using the position sensor may deviate from the intended predefined location, thereby, may result in inaccurate registration.

The inventors found that the shorter the distance between the predefined locations on skin 52 and the respective closest bone tissue, the higher the accuracy of the position acquired by the position sensor of wand 30. In some embodiments, processor 34 is configured to assign a weight to each of the predefined locations based on the respective distance between the anatomical points and the closest bone tissue. The weight may be assigned inversely proportional to the value of the distance.

For example, distance 64A at location 56 is substantially smaller than distance 64C at location 60. In an embodiment, processor 34 is configured to assign a larger weight at location 56 compared to the weight assigned at location 60.

Similarly, the minimal distance between skin 52 and bone 54B is longer than minimal distance 64A and shorter than distance 64C. In an embodiment, processor 34 is configured to assign a weight at predefined location 58, which is larger than the weight assigned at location 60, and smaller than the weight assigned at location 56.

In some embodiments, the distance (e.g., distance 64A) is calculated as a Euclidean distance vector in a 3D coordinate system. In an embodiment, the distance vector may be calculated in a Cartesian coordinate system, and therefore, may comprise three components of the respective x, y, and z axes. In this embodiment, at a location marked (e.g., in equation (2) below) by an index "i", processor 34 is configured to assign weights $a_i$, $b_i$ and $c_i$, for the distance vector components of x, y, and z axes, respectively.

Registering Coordinate Systems Based on Bone Proximity to Predefined Location

In some embodiments, the anatomical points acquired on skin 52, e.g., at predefined locations 56, 58 and 60, are referred to as "CT frame of reference (CFOR)" in the coordinate system of the CT system. Similarly, the positions acquired at the same locations (e.g., locations 56, 58 and 60), in the coordinate system of the position tracking system, are referred to as "position frame of reference (PFOR)."

In some embodiments, registration between the CFOR and PFOR systems may be carried out using any suitable method, such as an iterative closest point (ICP).

The ICP method iteratively applies a transformation (translation and/or rotation) for finding a best mapping between the coordinate systems.

At each predefined location, the distance vector between the anatomical point and the corresponding position point, is given by equation (1):

$$d_{position} = \|p_{position} - q_{position}\| \quad (1)$$

wherein $d_{position}$ the distance vector between an anatomical point and a corresponding position at each predefined location;

$p_{position}$ is the position of the anatomical point (e.g., point 62A) in the CFOR system; and $q_{position}$ is the position acquired by the position sensor (e.g., location 56) in the PFOR system.

In some embodiments, processor 34 is configured to register the coordinate systems of the CT and the position tracking systems, by correlating between the positions and the respective anatomical points, e.g., using a weighted least squares minimization procedure. In an embodiment, processor 34 is further configured to apply the assigned weights to every component (e.g., x, y, and z) of the distance vector at every predefined location, as given by equation (2):

$$d_{position} = \sqrt{a_i(p_{x_i} - q_{x_i})^2 + b_i(p_{y_i} - q_{y_i})^2 + c_i(p_{z_i} - q_{z_i})^2} \quad (2)$$

wherein $a_i$, $b_i$ and $c_i$ are the assigned weights at a predefined location marked by an index "i" for the x, y, and z coordinates, respectively;

$p_{x_i}$, $p_{y_i}$ and $p_{z_i}$ are components of the position of an anatomical point at x, y, and z coordinates, respectively; and $q_{x_i}$, $q_{y_i}$ and $q_{z_i}$ are components of the position acquired by the position sensor at x, y, and z coordinates, respectively.

Note that the values of $a_i$, $b_i$ and $c_i$ are calculated based on the components of the distance vector (e.g., distance 64A) between the anatomical point at the predefined location (e.g., CT point 62A at location 56) and the closest bone tissue (e.g., bone 54A).

Figure 3:
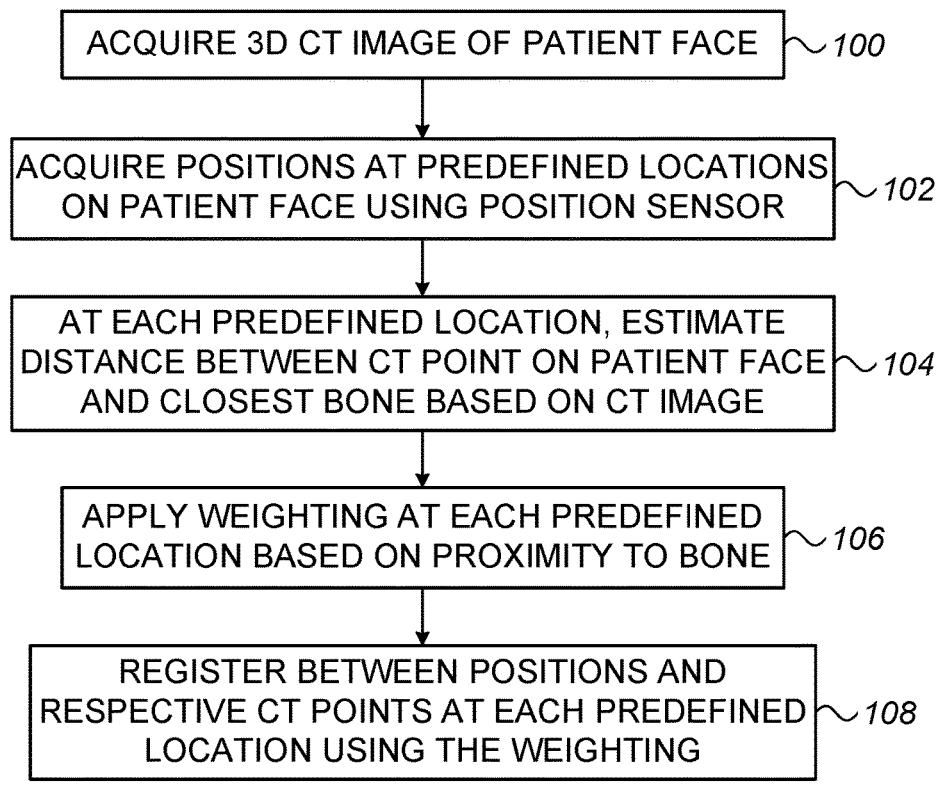
FIG. 3 is a flow chart that schematically illustrates a method for registering a coordinate system of a magnetic position tracking system with that of a pre-acquired computerized tomography (CT) image, in accordance with an embodiment of the present invention.

FIG. 3 is a flow chart that schematically illustrates a method for registering the coordinate system of the magnetic position tracking system with the coordinate system of a CT imaging system, in accordance with an embodiment of the present invention.

The method begins with an image acquisition step 100, in which an operator (e.g., physician 24) acquires 3D anatomical image 50 of the face of patient 22, using the CT system, or any other suitable imaging system. In some embodiments, processor 34 is configured to display bone tissue of the face and multiple CT points, such as points 62A and 62C, at the respective predefined locations (e.g., locations 56 and 60) of image 50. At a position acquisition step 102, physician 24 attaches wand 30, which comprises the position sensor, to each of the predefined locations, so as to acquire the respective positions in the coordinate system of the position tracking system.

At a distance calculation step 104, processor 34 identifies the predefined locations in image 50, and calculates, at each predefined location, the distance between a respective CT point and the closest bone tissue, as described above.

At a weights assignment step 106, processor 34 assigns weights to each of the predefined locations, based on the respective distances between the CT points and the closest bone tissue. For example, the value of distance 64A is smaller than the value of distance 64C, therefore, the value of the weight at predefined location 56 (the forehead) is higher than the value of the weight at predefined location 60 (the cheek).

At a registration step 108, processor 34 registers between the coordinate systems of the CT and the position tracking systems, by correlating between the positions acquired by the position sensor at the predefined locations, and the respective CT points, using the respective weights assigned to each predefined location.

Note that the value of the weight at the forehead is larger than the value of the weight at the cheek, therefore, the weight at predefined location 56 has higher impact on the registration than the weight at predefined location 60.

In an embodiment, processor 34 carries out the registration by applying a suitable method that iteratively minimizes the sum of distances between pairs of points of the CFOR and PFOR systems, such as the iterative closest point (ICP) method. Further details of the ICP method are provided, for example, by Rusinkiewicz et al., in "Efficient Variants of the ICP Algorithm," proceedings of the third international conference on 3-D Digital Imaging and Modeling, Pages 145-152 (2005); and by Chen et al., in "Object Modeling by Registration of Multiple Range Images," proceedings of the IEEE conference on robotics and automation, Pages 2724-2729, vol. 3 (1991), which are both incorporated herein by reference. In brief, the ICP method typically comprises the following six stages: 1. Selection of some set of points in one or both meshes; 2. Matching these points to samples in the other mesh; 3. Weighting the corresponding pairs appropriately; 4. Rejecting certain pairs based on looking at each pair individually or considering the entire set of pairs; 5. Assigning an error metric based on the point pairs; 6. Minimizing the error metric."

Although the embodiments described herein mainly address sinuplasty applications, the methods and systems described herein can also be used in other applications, such as in other Ear-Nose-Throat (ENT) applications and orthopedic applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A method, comprising:
    identifying, in a three-dimensional (3D) anatomical image of a patient head, multiple anatomical points corresponding to respective predefined locations on a skin of the patient head in a first coordinate system;
    receiving multiple positions in a second coordinate system, measured by a position sensor of a position-tracking system at the respective predefined locations on the skin of the patient head;
    calculating, at each predefined location, a distance between a respective anatomical point and closest bone tissue of the patient head;
    assigning weights to the predefined locations based on respective distances between the anatomical points and the closest bone tissue, wherein assigning the weights comprises assigning a first weight to a first predefined location having a first distance to the closest bone tissue, and assigning a second weight, larger than the first weight, to a second predefined location having a second distance to the closest bone tissue, smaller than the first distance; and
    registering the first and second coordinate systems, by correlating between the positions and the respective anatomical points using the assigned weights, wherein registering the first and second coordinate systems comprises calculating a transformation between the first and second coordinate systems, in which the second predefined location has higher impact than the first predefined location.

2. The method according to claim 1, wherein the 3D anatomical image comprises a computerized tomography (CT) anatomical image.

3. The method according to claim 1, wherein receiving the multiple positions comprises receiving positions located at the predefined locations on the patient head.

4. The method according to claim 1, wherein receiving the multiple positions comprises receiving the positions from a registration tool comprising the position sensor.

5. The method according to claim 1, wherein calculating the distance comprises calculating a Euclidean distance vector having multiple components.

6. A method, comprising:
    identifying, in a three-dimensional (3D) anatomical image of a patient head, multiple anatomical points corresponding to respective predefined locations on a skin of the patient head in a first coordinate system;
    receiving multiple positions in a second coordinate system, measured by a position sensor of a position-tracking system at the respective predefined locations on the skin of the patient head;
    calculating, at each predefined location, a distance between a respective anatomical point and closest bone tissue of the patient head;
    assigning weights to the predefined locations based on respective distances between the anatomical points and the closest bone tissue, wherein assigning the weights comprises assigning a weight to each respective component of the Euclidean distance vector; and
    registering the first and second coordinate systems, by correlating between the positions and the respective anatomical points using the assigned weights, wherein registering the first and second coordinate systems comprises using, at each predefined location, the assigned weights to each of the respective components.

7. An apparatus, comprising:
    a registration tool, which comprises a position sensor of a position-tracking system, which is configured to acquire multiple positions in a second coordination system by positioning the registration tool at respective predefined locations on a skin of a patient head; and
    a processor, which is configured to:
        identify, in a three-dimensional (3D) anatomical image of the patient head, multiple anatomical points corresponding to the respective predefined locations in a first coordinate system;
        receive the multiple positions measured in the second coordinate system;
        calculate, at each predefined location, a distance between a respective anatomical point and closest bone tissue of the patient head;
        assign weights to the predefined locations based on respective distances between the anatomical points and the closest bone tissue, by assigning a first weight to a first predefined location having a first distance to the closest bone tissue, and a second weight, larger than the first weight, to a second predefined location having a second distance to the closest bone tissue, smaller than the first distance; and
        register the first and second coordinate systems, by correlating between the positions and the respective anatomical points using the assigned weights, by calculating a transformation between the first and second coordinate systems, in which the second predefined location has higher impact than the first predefined location.

8. The apparatus according to claim 7, wherein the 3D anatomical image comprises a computerized tomography (CT) anatomical image.

9. The apparatus according to claim 7, wherein the patient organ comprises a patient head, and wherein the processor is configured to receive positions located at the predefined locations on the patient head.

10. An apparatus comprising:
    a registration tool, which comprises a position sensor of a position-tracking system, which is configured to acquire multiple positions in a second coordination system by positioning the registration tool at respective predefined locations on a skin of a patient head; and
    a processor, which is configured to:
        identify, in a three-dimensional (3D) anatomical image of the patient head, multiple anatomical points corresponding to the respective predefined locations in a first coordinate system;
        receive the multiple positions measured in the second coordinate system;

calculate, at each predefined location, a distance between a respective anatomical point and closest bone tissue of the patient head by calculating a Euclidean distance vector having multiple components;

assign weights to the predefined locations based on respective distances between the anatomical points and the closest bone tissue; and register the first and second coordinate systems, by correlating between the positions and the respective anatomical points using the assigned weights.

11. The apparatus according to claim 10, wherein the processor is configured to assign a weight to each respective component of the Euclidean distance vector, and to use, at each predefined location, the assigned weights to each of the respective components.

* * * * *